United States Patent [19]

Kalentun et al.

[11] Patent Number: 6,040,494
[45] Date of Patent: Mar. 21, 2000

[54] FOAM MATERIAL ITS MANUFACTURING METHOD AND USE AND AN ABSORBENT DISPOSABLE ARTICLE COMPRISING SUCH A FOAM MATERIAL

[75] Inventors: Pia Kalentun; Anette Buschka, both of Göteborg; Andrea Schmid, Mölnlycke; Eva Strömbom, Mölndal, all of Sweden

[73] Assignee: SCA Hygiene Products AB, Gothenburg, Sweden

[21] Appl. No.: 09/076,071

[22] Filed: May 12, 1998

[30] Foreign Application Priority Data

May 15, 1997 [SE] Sweden .................................. 9701807

[51] Int. Cl.[7] .............................. A61F 13/15; C08J 9/26; C08J 9/28
[52] U.S. Cl. .............................. 604/369; 521/62; 521/63; 521/64; 428/304.4
[58] Field of Search ..................................... 604/369, 358, 604/359; 521/61, 62, 63, 64; 428/304.4

[56] References Cited

U.S. PATENT DOCUMENTS

| | | |
|---|---|---|
| 5,331,015 | 7/1994 | DesMarais et al. . |
| 5,387,207 | 2/1995 | Dyer et al. . |
| 5,500,451 | 3/1996 | Goldman et al. . |

FOREIGN PATENT DOCUMENTS

| | | |
|---|---|---|
| WO 93/04092 | 3/1993 | WIPO . |
| WO 93/04093 | 3/1993 | WIPO . |
| WO 93/04113 | 3/1993 | WIPO . |
| WO93/04115 | 3/1993 | WIPO . |
| WO 93/21234 | 10/1993 | WIPO . |
| WO 94/13704 | 6/1994 | WIPO . |

*Primary Examiner*—John G. Weiss
*Assistant Examiner*—Carie Mager
*Attorney, Agent, or Firm*—Burns, Doane, Swecker & Mathis, L.L.P.

[57] ABSTRACT

The invention pertains to a foam material for absorption of aqueous liquids, a manufacturing method and an advantageous use of such a foam material, and an absorbent disposable article comprising such a foam material. The foam material is hydrophilic and primarily intended for use in absorbent disposable articles such as baby diapers, incontinence protectors and products for feminine hygiene. However, the foam material according to the invention is also suited for use in other absorbent articles, such as in different wiping materials, bandage materials and other similar products. The chemical structure of a surfactant, which is utilized as a combined emulsifying and hydrophilizing agent when manufacturing the foam material according to the invention, makes it possible to retain a sufficient proportion of the foam surfactant in the foam material even after repeated wettings, something which renders the foam material highly, permanently hydrophilic.

13 Claims, 2 Drawing Sheets

FOAM MATERIAL ITS MANUFACTURING METHOD AND USE AND AN ABSORBENT DISPOSABLE ARTICLE COMPRISING SUCH A FOAM MATERIAL

TECHNICAL FIELD

The present invention pertains to a foam material for absorption of aqueous liquids and a manufacturing method for such a foam material. The present invention further indicates an advantageous use of the foam material and provides an absorbent disposable article comprising a foam material according to the invention.

The foam material according to the invention is hydrophilic and is primarily intended for use in absorbent disposable articles such as baby diapers, incontinence protectors and products for feminine hygiene. The foam material according to the invention, however, is also suitable for use in other absorbent articles, for example in different wiping materials, bandage materials and other similar products.

BACKGROUND OF THE INVENTION

The development of absorbent disposable articles, such as baby diapers, incontinence protectors and products for feminine hygiene, has recently to a high degree been directed towards the development of thinner and thinner products. The reason why the product development has taken this direction is, for example, that a thinner diaper is more comfortable to wear, and that it is perceived as being more discreet to the user. Furthermore, a thinner product results in a lower distribution cost and a lower environmental load per article in connection with the transports which are required in order to enable the product to reach the enduser.

The possibilities to gradually provide thinner absorbent articles are dependent on the ability to develop thinner and thinner absorption cores or absorption structures, which can receive and store large quantities of human exudates, such as urine or other body fluids.

Thereby, particle-shaped absorbent polymers, often referred to as superabsorbents, have been particularly valuable in order to enable this development. A commonly occurring type of superabsorbents is polyacrylates with a relatively low degree of cross-linking.

The absorption mechanism of superabsorbents of polyacrylate type is based on the fact that the lightly cross-linked polymers comprise a plurality of anionic carboxylate groups which are attached to the polymer chain. These charged carboxylate groups enable the polymer to absorb aqueous liquids by means of osmotic forces.

Another important mechanism, when absorbent articles are concerned, is absorption based on capillary forces. Examples of capillary absorbents are different fibre-based materials such as fluff pulp, tissue paper or different types of nonwoven materials. In some cases, capillary absorbents can be superior to the above-mentioned absorbents acting by means of osmotic forces. Accordingly, the absorption and distribution rates are in general higher for capillary absorbents than for superabsorbents. By means of placing capillary absorbents, having a certain fibre orientation, capillary size or hydrophilic character in suitable positions in an absorbent article, the absorbed liquid may further be directed in the desired direction.

As a consequence, many previously known absorbent articles combine capillary absorbents with superabsorbents, acting by means of osmotic forces, with good results.

In the following, such an advantageous previously known combination is exemplified by an imaginary absorbent body intended for use in a baby diaper.

The imaginary absorbent body is covered with a hydrophobic surface material, having relatively large capillaries, on the side of the absorbent body which is intended to be facing towards a wearer. This surface layer has the ability to rapidly let trough for example urine to underlying material layers, and remains dry thanks to its hydrophobic nature, something which is an advantage, amongst other things when comfort is concerned.

An acquisition layer, e.g. a cellulose wadding, is arranged inside the surface material of the imaginary absorbent body. The function of the acquisition layer is to receive and distribute absorbed liquid in the absorbent body in order to thereby obtain a better utilization of the total storage capacity of the absorbent body.

An absorbent core, consisting of a mixture of fluff pulp fibres and superabsorbent, follows inside the acquisition layer of the imaginary absorbent body. Inside the core, the pulp fibres so to speak form a fibre matrix which distributes the liquid in the core by means of capillary forces, so that the superabsorbent particles gradually can absorb and store the liquid by means of osmotic forces.

Absorbent articles of the "combination type" described in the example above, however, are proportionately expensive and complicated to manufacture, since they contain a number of different material types. Another disadvantage is that problems with the integrity of the absorbent core easily may arise during use, so that the core gradually ruptures or goes lumpy. Another difficulty is to be able to distribute and retain the superabsorbent in a desired way in the absorbent core until the absorbent article has been used.

Another problem, which may arise with combination products comprising both fluff pulp and superabsorbents, is so-called gel-blocking. This problem arises because superabsorbent particles, which have absorbed liquid locally, form a gel. This results in the capillary liquid transport via the fibre matrix being blocked and therefore causes a collection of liquid in certain portions of the absorbent body, whereas the absorption capacity in other portions remains more or less unemployed.

In light of the above-mentioned problems, it has previously been suggested that another type of absorbent material should be used in absorbent articles, that is polymeric foams with open cells.

Such previously known foam materials can be manufactured by means of using the manufacturing method which is disclosed in the patent publication WO 93/21234. The therein disclosed manufacturing method provides porous, cross-linked polymeric foam materials having a low density.

According to WO 93/21234, the manufacturing method comprises a "water-in-oil" emulsion polymerization of monomers which comprise at least one vinyl monomer, a difunctional unsaturated cross-linking monomer, at least 90 weight-% water calculated on the emulsion, a first surfactant comprising a sorbitan monoester having a fatty acid moiety of at least 6 carbon atoms, and at least one second sorbitan ester having at least one different fatty acid moiety than the first surfactant, and a polymerization catalyst. The method is claimed to provide open-cellular foams with low density, high absorption capacity and good physical properties in this way.

In the above-mentioned WO 93/21234 it is disclosed that the internal water phase during polymerization preferably contains a water soluble electrolyte, amongst other things in order to make the foam more water wettable to. Suitable electrolytes for this purpose are stated to be inorganic salts (monovalent, divalent, trivalent or mixtures thereof), such as alkali metal salts, alkaline metal salts, and heavy metal salts such as halides, sulphates, carbonates, phosphates and mixtures thereof. The electrolytes can also include sodium chloride, sodium sulphate, potassium chloride, potassium sulphate, lithium chloride, magnesium chloride, calcium chloride, magnesium sulphate, aluminium chloride and mixtures of these. Mono- or di-valent metal salts with monovalent anions are stated to be preferred.

Foam materials of the type disclosed in WO 93/21234 can provide both capillary liquid absorption, transport and storage and should therefore be suitable for use as absorption cores in absorbent articles, for example diapers.

Accordingly, the patent publication WO 93/04092 discloses absorbent foam materials for absorption of aqueous body fluids. The foam materials disclosed in WO 93/04092 are said to be suitable for use in absorption cores of absorbent articles, for example diapers.

The foam materials according to WO 93/04092 comprise hydrophilic, flexible structures with open cells which preferably are prepared by means of polymerizing "water-in-oil" emulsions. Such emulsion are usually referred to as HIPE-emulsions (High Internal Phase Emulsions).

According to WO 93/04092, HIPE-emulsions can be formed by means of intense agitation of a polymerizable mixture containing a relatively small amount of a polymerizable monomer-containing oil phase and a, relatively, larger amount of a relatively monomer-free water phase. In the emulsion, this discontinuous, "internal" water phase forms a network of dispersed "droplets", which are surrounded by the continuous, polymerizable oil phase with therein dissolved surfactant. During the polymerization of the monomers in the continuous oil phase, a cellular foam structure is formed. After polymerization, the aqueous liquid remaining in the foam structure formed upon polymerization can be removed by pressing and/or drying the foam. If necessary, the polymerized foam material can be subjected to different types of post-treatment, for example a hydrophilizing treatment.

In WO 93/04092, a number of different parameters are mentioned which are essential for deciding structural, mechanical and functional parameters of a foam material.

Accordingly, it is disclosed that the relative amounts of water and oil phase which are used in order to form the polymeric foam can affect foam density, the cell size and the specific surface of the pores which form the foam. In WO 93/04092 it is disclosed that the ratio between water and oil phase suitably is between 12:1 and 100:1, more preferably between 20:1 and 70:1, and most preferably 25:1 to 50:1.

According to WO 93/04092, the continuous oil phase of the emulsions comprises the polymers which are to form the solid foam structure. The monomers are said to include three different components; principal monomer, comonomer and cross-linking agent. The principal monomer is said to comprise one or more monomers that tend to impart glass-like properties to the resulting foam structure. After polymerization, such monomer materials are said to produce homopolymers with high molecular weight (>6000) and a glass transition temperature $T_g$ about 40° C. or higher. As preferred "glass-like" monomers, inter alia, non-substituted or substituted styrenes are mentioned. The addition is said to normally be between 3–41%, more preferably 7–40 weight-% of the oil phase.

The above-mentioned comonomer component is claimed to comprise one or several comonomers, which tend to impart "rubber-like" properties to the resulting foam structure. This type of comonomers are said to be monomers which would provide homo polymers with a high molecular weight (>10000) and a glass transition temperature of about 40° C. or lower. Monofunctional, "rubber-like" comonomers of this type are said to comprise, for example, alkyl-acrylates, alkyl-methacrylates, allyl-acrylate, butadiene, substituted butadienes, vinylidene halides and combinations of such. Preferred "rubber-like" co-monomers are said to include; butylacrylate, 2-ethylhexylacrylate, butadiene, isoprene and combinations of these. Butylacrylate and 2-ethylhexylacrylate are stated to be the most preferred. The monofunctional "rubber-like" comonomer component is said to normally constitute up to 27–73%, more preferably from about 27–66 weight-% of the oil phase.

(In connection with this, it might be mentioned that it is generally accepted that glass transition temperatures $T_g$<25° C. result in rubber-like properties at room temperature, for example, polymers comprising 2-ethylhexylacrylate have $T_g$=−70° C. and are therefore clearly rubber-like at room temperature).

In WO 93/04092 it is disclosed that the molar ratio between the "glass-like" monomer component and the "rubber-like " component" in general is between 1:25 to 1.5:1, more preferably from about 1:9 to 1.5:1.

In order to make it possible to obtain a polymerization, the HIPE-emulsions disclosed in WO 93/04092 are said to also require the presence of a poly-functional cross-linking agent in the oil-phase. Thereby, the selection of cross-linking agent is said to be of great importance for achieving the desired properties of the finished foam. The It is disclosed that the cross-linking agent can be selected from a great number of polyfunctional, preferably difunctional monomers, for example aromatic divinyls such as divinylbenzene, divinyltoluene or diallylphthalate. Alternatively, aliphatic cross-linking agents of divinyl type are said to be useful, such as diacrylic acid esters of polyols. However, the most preferred cross-linking agent is claimed to be divinylbenzene. Suitable addition levels are said to be 8–40%, more preferably 10 to 25 weight-% of the oil phase.

According to WO 93/04092, it is of outermost importance that the above-mentioned monomers, comonomers and cross-linking agents are substantially water-insoluble, so that they are primarily soluble in the oil phase and not in the water phase. Furthermore, the importance of the raw materials used during the foam preparation being non-toxic and chemically stable is underlined.

According to WO 93/04092, another essential component of the oil phase of HIPE-emulsions is an emulsifier, which permits the formation of a stable HIPE-emulsion. Such emulsifiers are soluble in the oil phase and are said to be nonionic, cationic or anionic, as long as they are able to form a stable emulsion. Preferred emulsifiers are said to be sorbitan fatty acid ethers, polyglycerol fatty acid esters, polyoxyethylene (POE), fatty acids and esters. Sorbitan monolaurate, sorbitan monooleate and combinations of sorbitan trioleate and sorbitan monooleate are mentioned as particularly preferred. Other preferred emulsifiers are said to be polyglycerol ester and sorbitan sesquioleate. The emulsifier is said to normally constitute about 2–33 weight-%, more preferably 4–25 weight-% of the oil phase. In WO 93/04092, it is disclosed that the oil phase, in addition to the above-mentioned monomers and emulsifiers, also may contain further optional components. Examples of such are said to be oil soluble polymerization initiators or solvents for solving monomers and emulsifier in the oil phase.

According to WO 93/04092, the discontinuous, internal water phase in a HIPE-emulsion is an aqueous solution, which in general contains one or more dissolved components. An essential such component is said to be a water soluble electrolyte, the task of which is to minimize the tendency of monomers and cross-linking agents, which are primarily oil soluble, to also dissolve in the water phase. This is said to be important in order to minimize the risk of polymeric material filling the cells which are formed by the water phase droplets in the emulsion, something which could impair the resulting foam quality.

The above-mentioned electrolyte can allegedly be of any type that provides ionic strength to the water phase. Preferred electrolytes are said to be mono-, di-, or tri-valent inorganic salts, such as water soluble halides, e.g. chlorides, nitrates and sulphates of alkali metals or alkaline earth metals. Sodium chloride, calcium chloride, sodium sulphate and magnesium sulphate are mentioned as examples, with calcium chloride as the most preferred. The electrolyte addition is said to be between 0.2–40% in general, more preferably from about 0.5–20 weight-% of the water phase.

From WO 93/04092, it is further evident that a polymerization initiator usually is added to the water phase. Such an initiator is said to be any conventional water-soluble initiator of free radicals. The initiator is said to consist of compounds such as sodium, ammonium and ammoniumpersulphates, caprylyl peroxide, benzoyl peroxide, hydrogen peroxide, cumene hydroperoxides, tertiary butyldiperphtalate, tertiary butylperbensoate, sodium peracetate, sodium percarbonate and the like. Also conventional redox initiator systems are said to be useful, by means of combining the above-mentioned peroxygen compounds with reducing agents, such as sodium bisulphite, L-ascorbic acid or ferrous salts. The initiator is said to constitute up to about 5 mole-%, more preferably 0.001–0.5 mole-%, based on the total number of moles of polymerizable monomers in the oil phase. When addition to the water phase is concerned, this is said to involve contents of 0.02–0.4%, more advantageously from about 0.1–0.2 weight-% of the water phase.

WO 93/04092 discloses that the above-mentioned oil and water phases are combined during agitation in order to form a stable emulsion, after which the emulsion is subjected to polymerization conditions which are suitable to bring about polymerization of the monomers in the oil phase and thereby to form a solid cellular foam structure.

From WO 93/04092, it is evident that the therein disclosed foam material has a hydrophobic character immediately after the polymerization. Since the intended use requires a hydrophilic material, the foam material has to be treated after the polymerization in order to render the surfaces of the material more hydrophilic. This hydrophilizing treatment is said to be accomplished by means of treating the foam structure with a suitable hydrophilizing agent.

According to WO 93/04092, the hydrophilizing agent may be any material, having the ability to enhance the wettability to water of the polymer surfaces. Such previously known agents are said to include surface-active materials, surfactants, of anionic, cationic or nonionic type. Hydrophilizing agents are said to normally be employed in liquid form, thereby dissolved in water in order to form an aqueous hydrophilizing solution which is applied onto the surfaces of the foam material. It is claimed that a sufficient amount of hydrophilizing agent can be absorbed in this way, in order to render the foam surfaces sufficiently hydrophilic, without affecting the flexibility and compressibility properties of the foam material. The content of hydrophilizing agent, which has been incorporated into the foam structure, is said to suitably be between 0.1–10 weight-% of the foam.

Suitable hydrophilizing agents are claimed to comprise mild, non-irritating surfactants which are applied on the foam structure in amounts which are sufficient in order to result in a surfactant content from about 0.5–5.0%, more preferably from about 1–3 weight-% of the foam.

As examples of suitable surfactants, WO 93/04092 mentions alkyl sulphates and alkylethoxylated sulphates of the type which is used in commercial washing-up detergents. Aqueous solutions of such surfactants are said to typically be used for washing the foam structure, either residual water material after the foam polymerization, or more preferably as part of a washing treatment that serves to remove this residual water phase material.

Another preferred type of hydrophilizing agents are said to be hydratable, and preferably hygroscopic or deliquescent, water soluble inorganic salts, such as alkaline earth metal salts. Preferred salt types are claimed to be calcium and magnesium halides, such as calcium chloride. It is stated that salts of this type can be easily incorporated in the absorbent foam materials by means of treating the foam materials with solutions of such salts.

In the same way as mentioned above when surfactants are concerned, it is disclosed that the hydrophilizing treatment either can be performed after water phase residues from the polymerization having been removed, or as a part of the process of removing the residual water phase from the recently polymerized foam. Preferred salt contents are claimed to be from about 0.1–7 weight-% of the foam material.

From WO 93/04092, it is evident that the hydrophilizing treatment is performed to the extent it is necessary on HIPE-foam materials, which after polymerization are comparatively hydrophobic to their nature.

In WO 93/04092, it is also disclosed that some HIPE-foam materials can be sufficiently hydrophilic directly after the polymerization, and that such materials therefore do not need any subsequent hydrophilizing treatment. As examples of such materials HIPE-foams are mentioned, wherein sorbitan fatty acid esters have been used as an emulsifier additive in the oil phase, and wherein calcium chloride has been used as an electrolyte in the water phase. It is claimed that the content of calcium chloride in the residual water phase of such materials, after the polymerization, is sufficiently high in order to render the internal surfaces of the foam material, which also contain emulsifier residues, suitably hydrophilic also after dewatering of the polymerized foam.

There are a further number of patent publications which disclose the preparation of hydrophilic foam materials of the above-discussed type, or materials of a similar type.

Among these, the patent publication WO 93/00493 can be mentioned, disclosing a process for continuous preparation of HIPE-emulsions which are suitable for subsequent polymerization into polymeric foam materials, that upon dewatering act as absorbents for aqueous body fluids. The process involves continuous addition of a certain type of monomer-containing oil phase and a certain type of electrolyte-containing water phase to a dynamic mixing zone at relatively low water:oil ratios. The flow rates are steadily adjusted in order to increase the water:oil ratio of the streams which are fed to the continuous mixing zone, while the content in the dynamic mixing zone is subjected to a shear agitation which is sufficient in order to form a HIPE-emulsion, that upon subsequent polymerization provides a foam which has an average cell size from about 5 to 100 micrometer. The formation of such a stable HIPE-emulsion is completed by feeding the contents in the dynamic mixing zone to and through a static mixing zone.

In WO 93/04093, a number of different emulsifiers are mentioned which are claimed to be useful for creating a stable HIPE-emulsion. The emulsifiers are claimed to be nonionic, cationic, anionic or amphoteric, depending on the other conditions. Sorbitan fatty acid esters, polyglycerol fatty acid esters, polyoxy-ethylene fatty esters and esters are disclosed as particularly preferred emulsifiers.

In WO 93/04093, it is further disclosed that the foam materials prepared by means of the therein described process, generally, should be subsequently treated in order to render the foam materials suitable as liquid absorbents. It is claimed that such a subsequent treatment can comprise a washing, in order to remove residual water phase from the cells of the foam, followed by a hydrophilizing treatment in order to render the surfaces of the foam more hydrophilic. Thereby, calcium chloride is disclosed as a suitable hydrophilizing agent.

WO 93/04113 is another patent publication within the field of hydrophilic foam materials. This publication discloses a method for rendering hydrophobic foams hydrophilic by means of treatment with simple surfactants and salts as hydrophilizing agents. In the disclosed method, a surfactant-containing foam is treated with a solution of, for example, calcium chloride and is thereafter dried in order to leave a uniformly distributed residue of hydrated or hydratable calcium chloride on the surfactant-containing internal foam surfaces. Also other hydratable calcium or magnesium salts, such as magnesium chloride, are claimed to be usable. The resulting hydrophilic foams are said to be suitable for use in absorbent devices, including diapers, sanitary napkins, bandages and the like.

Another patent publication within the discussed field is WO 93/04115. This discloses a method for hydrophilizing hydrophobic foams, such as polyurethane foams and polymerized "water-in-oil" emulsion foams, which are claimed to be possible to hydrophilize with sorbitan monolaurate, which after drying is said to leave an essentially uniform residue of sorbitan monolaurate on the internal foam surfaces. The resulting treated foams are said to become hydrophilic and, accordingly, become suitable for use in absorbent devices, including diapers, sanitary napkins, bandages and the like.

A further patent publication, WO 94/13704, pertains to an absorbent foam material for aqueous body fluids and a manufacturing process for the same. The patent publication discloses a relatively thin, collapsed/non-expanded polymeric foam material which, when in contact with aqueous body fluids, expands and absorbs the fluids. Furthermore, a process for obtaining such foam materials in a stable way is disclosed, by means of polymerizing a specific type of "water-in-oil" emulsion, normally known as a HIPE-emulsion.

The foam materials disclosed in WO 94/13704 are said to be hydrophilic to their nature. It is claimed that hydrophilic foam surfaces are obtained since residues of hydrophilizing agent have remained in the foam structure after the polymerization, or by means of a special subsequent treatment procedure, aimed at modifying the surface energy of the foam material.

An example of remaining residues of hydrophilizing agent in the foam structure, which is disclosed in WO 94/13704, is a toxilogically acceptable, hygroscopic, hydrated salt, which preferably is calcium chloride.

According to WO 94/13704, further examples of such residues of hydrophilizing agents are certain oil-soluble emulsifiers, for example sorbitan laureate.

In WO 94/13704, it is disclosed that both types of hydrophilizing agents either can be added as raw material for the foaming process or in a subsequent treatment step.

The patent publication U.S. Pat. No. 5,500,451 discloses a process for preparing HIPE-emulsions, which can be polymerized in order to provide flexible, micro-porous, open-celled polymeric foam materials. The prepared foam materials are claimed to be able to absorb aqueous liquids such as urine. It is disclosed that HIPE-emulsions can be manufactured by means of using certain aliphatic polyglycerol ethers as emulsifiers. It is claimed that these are chemically less complex and vary less in composition than many previously utilized emulsifiers for HIPE-emulsions. Furthermore, the polyglycerol ethers are claimed to have higher contents of surface-active components and lower contents of undesired components than previously utilized emulsifiers. It is claimed that the polyglycerol ethers provide emulsions with water droplets of a comparatively uniform size which are dispersed in the continuous oil phase.

The aliphatic polyglycerol ethers disclosed in U.S. Pat. No. 5,500,451, which are used as emulsifiers, are said to be selected from the group consisting of aliphatic glycerol ethers comprising at least about 40% linear, mono-aliphatic diglycerol ethers and at least about 60% polyglycerol ethers which have aliphatic groups within the region $C_{10}$–$C_{24}$. By means of utilizing aliphatic polyglycerol ethers with aliphatic groups within the region $C_{12}$–$C_{18}$, it is claimed that a hydrophilizing effect is maintained in the finished HIPE-foam also after washing and dewatering.

Accordingly, foam materials which are hydrophilic directly after the polymerization are previously known, as well as foam materials which have been hydrophilized by means of subsequent treatment with different surfactants or electrolytes. The use of such foam materials in disposable absorbent articles has also been previously suggested.

A disadvantage, which might be perceived with the previously known foam materials, however, is that there is a risk that the hydrophilizing agent, of some of the previously known types which have been mentioned in the foregoing is dissolved out of the foam material during wetting, in connection with the use of an absorbent disposable article. As a result of this, the foam material becomes less hydrophilic in repeated wettings, something which can be perceived as a disadvantage in many applications.

SUMMARY OF THE INVENTION

Accordingly, the first object of the present invention is to provide a hydrophilic, absorbent foam material, with low risk of dissolving out surfactant during wetting and with physical properties otherwise which makes the foam material suitable for use as an absorption core in absorbent disposable articles.

The second object of the present invention is to provide a manufacturing method for such a foam material.

Further objects of the present invention are to indicate an advantageous use of the foam material according to the invention, and to provide an absorbent disposable article comprising a foam material according to the invention in its absorption core or absorbent body.

In the course of their inventive work, the inventors of the present invention have surprisingly established that a hitherto, in this context, unknown surfactant is able to eliminate the above-mentioned disadvantage with previously known hydrophilic foam materials, and that foam materials, which according to the invention have been manufactured with the use of this surfactant as a combined emulsifying and hydrophilizing agent, furthermore provides otherwise excellent physical properties for use in absorbent disposable articles.

Accordingly, the above-mentioned objects of the present invention are achieved by means of the foam material according to the invention which, comprises a surfactant of the type nonionic block copolymer, and that the foam material according to the invention is utilized in absorbent disposable articles.

In accordance with the following claims 2, 6, 9 and 11, the surfactant most preferably comprises poly(12-hydroxystearic acid).

Thereby, the chemical structure of the nonionic block co-polymer makes it possible to retain a sufficient amount of the emulsifying agent inside the finished foam material according to the invention in order to obtain the desired, relatively permanent hydrophilic character without the need for any special hydrophilizing treatment, at the same time as the risk of dissolving out surfactant during wetting is minimized. A sufficient quantity of surfactant is retained in the foam material even if it is subjected to washing after completed polymerization, something which might be desirable in certain cases in order to remove undesired compounds such as residual monomers from the foam material.

The foam material according to the invention can be manufactured by means of utilizing the basic principles for preparation of so-called HIPE-emulsions, with subsequent polymerization of the oil phase, as has been described in the foregoing in connection with the prior art. Thereby, according to the invention, the above-mentioned surfactant of the type nonionic block copolymer is utilized as an emulsifying agent, instead of the above-discussed, previously known emulsifiers for HIPE-emulsions. When manufacturing foam materials according to the invention, the nonionic block co-polymer can be said to constitute a combined emulsifying and hydrophilizing agent.

When manufacturing foam materials according to the invention, styrene is preferably used in the oil phase as a "glass-like" monomer raw material, but also other suitable monomers can be utilized. To the glass-like monomer is also added a monomer which is able to lend "rubber-like" properties to the finished foam. This monomer is preferably 2-ethylhexyl acrylate, but many other monomers are conceivable for use in foam materials according to the invention.

A cross-linking agent, which preferably is divinylbenzene or other aromatic divinyl compounds, is also added to the oil phase, but also other previously known cross-linking agents can be utilized when manufacturing hydrophilic foam materials according to the invention.

When manufacturing foam materials according to the invention, a water phase comprising an initiator and a salt, which may be of any conventional previously known type, is utilized. The water phase and the above-mentioned oil phase are emulsified in the presence of the above-mentioned emulsifying agent, wherein the ratio water:oil always is larger than 1.

When desirable, foam materials according to the invention can be subjected to a washing treatment, according to prior art, after finished polymerization. After polymerization and possible washing treatment, follows a dewatering and/or drying, according to suitable previously known technique.

After dewatering, drying and possible washing treatment, finished foam materials according to the invention are sufficiently hydrophilic in order to provide good absorption and adsorption properties when absorbing aqueous liquids, for example body fluids.

The polymerized foam materials according to the invention have a foam structure which, when liquid absorption is initiated, comprises a plurality of essentially open cells which are in connection with each other for liquid transport.

Foam materials according to the invention have advantageous properties for use in absorbent disposable articles. Absorbent disposable articles according to the invention can be manufactured utilizing previously known techniques for the manufacture of this type of products, but with the difference that a foam material according to the invention entirely or partially replaces the conventional absorbent bodies which previously have been used.

In addition to foam materials according to the invention, absorbent disposable articles according to the invention comprise the other sub-components which are present in previously known products, for example a liquid-permeable surface material on the side which is intended to be facing towards a wearer, and a liquid-impermeable surface material on the side which is intended to be facing away from the wearer.

Furthermore, absorbent disposable articles according to the invention preferably comprise elastic means, for example in the form of waist linings and elastic leg cuffs. Furthermore, when desirable, absorbent disposable articles according to the invention can comprise attachment arrangements for simplifying their dressing onto a wearer, undressing, or adjustment of the size of the absorbent disposable article to the size of the wearer. Examples of such attachment arrangements are different systems with hook and loop strips, tape, hitches, crooks or the like.

Foam materials according to the invention can also be utilized for other forms of absorbent disposable articles than diapers and sanitary napkins, for example wiping cloths for cleaning and the like.

By means of pressing, vacuum packing or other compacting methods, foam materials according to the invention or absorbent disposable articles in which these are included can be compressed in order to facilitate storage and transportation. When foam materials according to the invention are utilized in, for example, absorbent disposable articles for absorption and storage of body fluids, the articles are preferably delivered in compressed form. When such a disposable article has been removed from its transport package and been brought into contact with the skin of a wearer, the cells of the integrated foam material according to the invention will once more have expanded to their essentially open positions because of the elastic nature of the foam material, from having been essentially compressed during the transport.

BRIEF DESCRIPTION OF THE DRAWINGS:

Results from measurements of acquisition time on foam materials prepared in laboratory scale are evident from the attached FIGS. 1 and 2. In the figures, test results for foam materials according to the invention are compared with results from measurements on foam materials according to prior art. The utilized test methods are described in connection with the following examples. In the attached drawings.

EXAMPLES AND PREFERRED EMBODIMENTS

Trials 1–5

Figure 1:
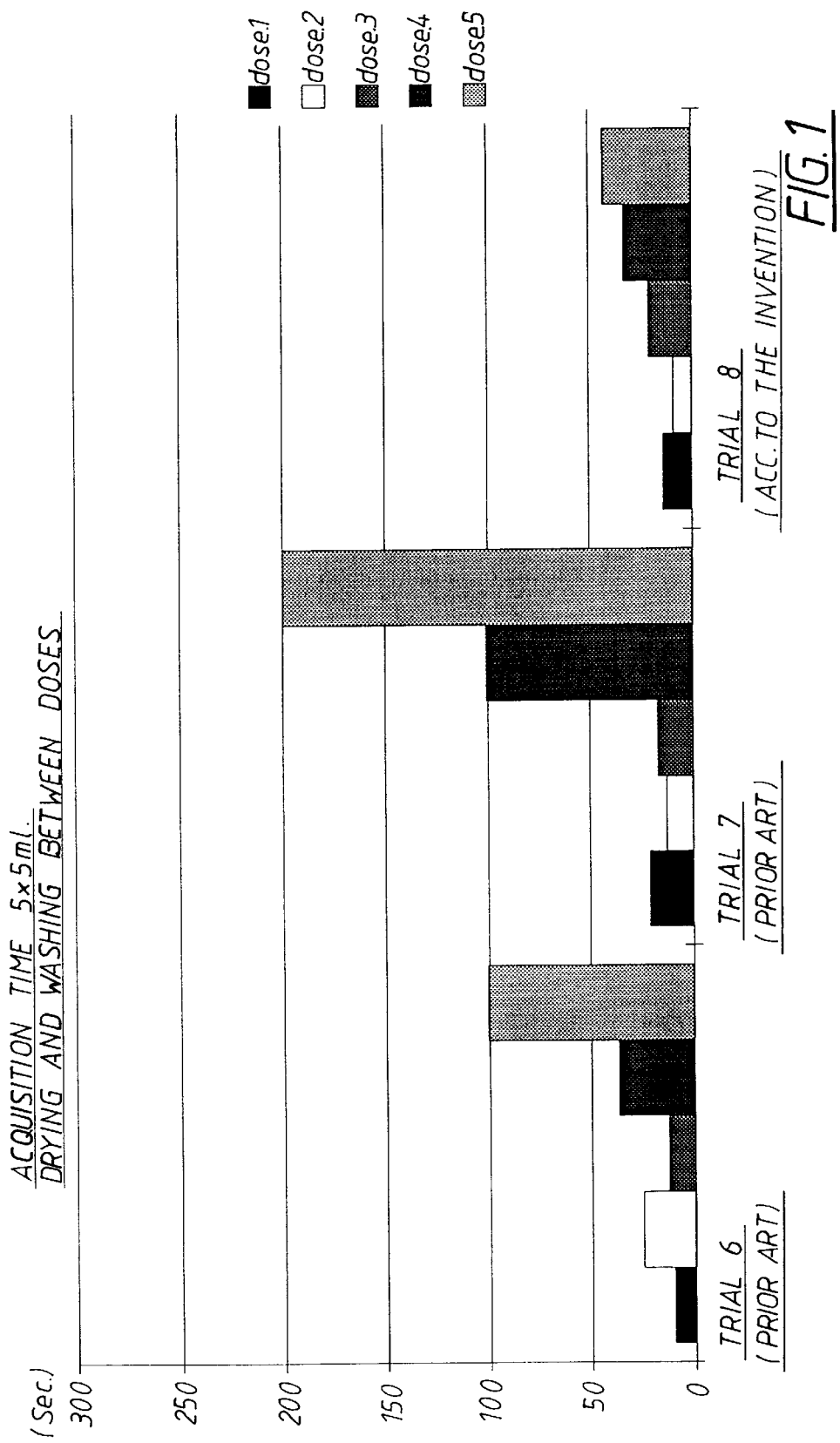
FIG. 1 shows a bar diagram presenting results from measurements of acquisition time on foam materials from trials 6 and 7 (acc. to prior art) and 8 (acc. to the invention), when absorbing 5 intermittent 5 ml doses of synthetic urine with intermediary washing in distilled water and drying between the doses.
Figure 2:
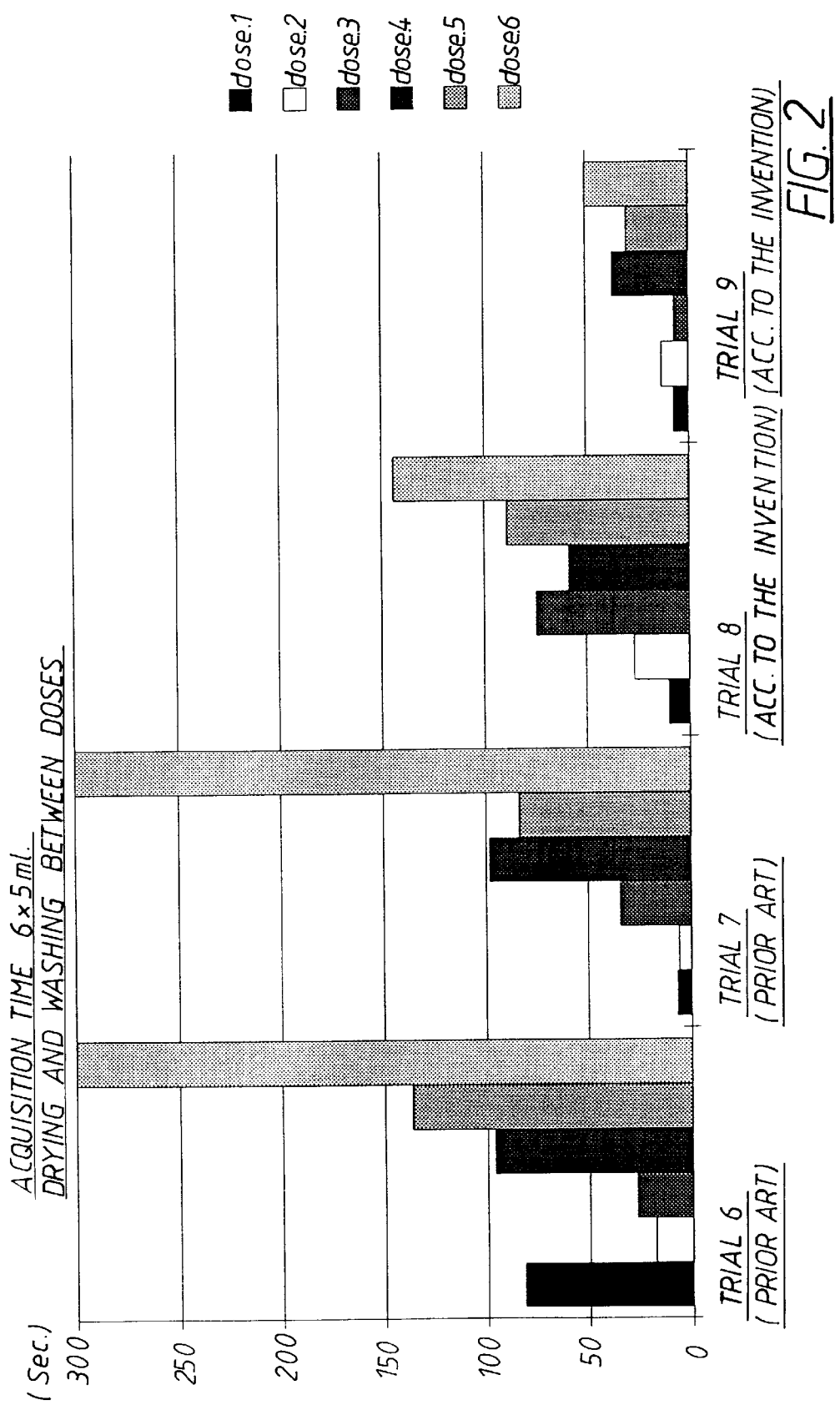
FIG. 2 shows a bar diagram presenting results from measurements of acquisition time on foam materials from trials 6 and 7 (acc. to prior art) and 8 and 9 (acc. to the invention), when absorbing 6 intermittent 5 ml doses of synthetic urine with intermediary washing in distilled water and drying between the doses.

In order to illustrate the invention, a number of foam materials were prepared; according to prior art, according to a preferred embodiment of the invention, and according to three advantageous embodiments of the invention.

When preparing a foam material according to prior art, the starting point in trial 1 was an oil phase comprising:

4 ml styrene
4 ml divinylbenzene
12 ml 2-ethylhexylacrylate
3 ml SPAN 80 (surfactant)
1 ml SPAN 85 (surfactant)

A 600 ml water phase, containing an initiator and a salt which both were of a conventional above-described type, was added to the oil phase, after which the mixture was transformed into a stable emulsion by means of intense agitation in a conventional way. Thereafter, the emulsion was polymerized in a heated oven during 18 h at 60° C. After finished polymerization, the obtained foam was washed with a water solution and dried.

Thereafter, a number of foam materials, for which a surfactant of the type nonionic block co-polymer was used, were prepared in trials 2 to 5 in a similar way as in trial 1. The surfactant which was used in the laboratory trials is marketed under the trademark Atlox and comprises poly(12-hydroxy-stearic acid). In trial 2, according to a preferred embodiment of the invention, solely poly(12-hydroxy-stearic acid) was used as emulsifying agent.

In trials 3, 4 and 5, which are according to advantageous embodiments of the invention, also conventional emulsifiers under the trademarks SPAN 80 and 85 were added in different additions, wherein SPAN 80 comprises sorbitan monooleate, while SPAN 85 comprises sorbitan trioleate.

Since the foam materials prepared in the laboratory trials all were of a type intended for use in applications where absorption of aqueous liquids occur, the finished foam materials were evaluated with respect to a number of physical properties essential to the application.

Thereby, a number of testing methods, which should be well-known to the man skilled in the art, were used, and are briefly described as follows.

Density, is determined as disclosed in the above-mentioned patent publication WO 93/04092 by means of a gravimetric procedure, in which the weight of a foam material specimen having a known volume is determined, whereafter the density is calculated and expressed in the unit $g/cm^3$. The utilized method essentially corresponds to ASTM Method: No. D3474-86.

Pore volume, is determined in the way disclosed in the above-mentioned WO 93/04092 under the headline "Available pore volume", by means of weighing dry foam specimens having a known volume, and saturating the specimens with isopropanol, and thereafter allowing excess liquid to run off and weighing the foam specimens. Thereafter, the weight of isopropanol in the saturated foam is calculated per weight unit of dry foam and is expressed in the unit g/g. Accordingly, the presented measurement values for "pore volume" actually correspond to "Measured Free Capacity, according to what is disclosed in WO 93/04092.

Compression resistance, is measured in the way disclosed in WO 93/04092, by means of measuring the compression (% thickness reduction) which is produced in a foam specimen which has been saturated with synthetic urine, after a load of 5.1 kPa having been applied onto the foam specimen.

Initial absorption, is measured on a test specimen having the measures 5×5 cm. A liquid droplet of 0.3 ml is applied onto the surface of the test specimen and the time needed for the droplet to be absorbed is recorded and presented in seconds.

Acquisition time, is a simple testing method which has proved to be suitable for evaluating different absorption properties of foam materials. The testing method can be modified in different ways depending on the application. According to the basic method for acquisition time, a test cylinder having a diameter of 23 mm is placed on top of a foam material specimen having a defined area. Thereby, the foam material is placed on a planar surface which does not absorb the synthetic urine which is to be used as absorption liquid during the measurement. A desired amount of liquid is gradually poured into the cylinder, so that a liquid column having a constant height of about 20 mm is maintained until the desired amount of liquid has been poured into the cylinder and absorbed by the foam material. The time consumed for the liquid column to be absorbed by the material specimen is recorded. By means of adding an additional liquid dose to the cylinder after a certain waiting time, and thereby once again record the acquisition time, valuable information concerning the behaviour of the foam material in repeated wettings can be obtained. An alternative measurement method, which for example is suited for evaluating the permanency of a hydrophilizing treatment, is to perform repeated measurements on a material specimen, and to subject the material specimen to washing with distilled water and drying between each measurement of acquisition time. The acquisition time is presented in seconds or minutes.

Acquisition time 3×60 ml, was measured on a foam material specimen with an area of 10×28 cm, wherein 60 ml doses of synthetic urine were added to the test cylinder in 3 rounds with 10 minutes intervals between each dose. The acquisition time in minutes was recorded for each dose.

Acquisition time 5×5 ml, was measured on a foam material specimen with an area of 5×5 cm. Doses of 5 ml synthetic urine were added to the test cylinder in 5 rounds. The test specimen was subjected to washing with distilled water and drying between each additional dose. The acquisition time in seconds was recorded for each dose.

Acquisition time 6×5 ml, was measured in the corresponding way as acquisition time 5×5 ml, but with the difference that 6 doses of synthetic urine were used instead of 5.

Rewetting, also provides valuable information about the absorption properties of a foam material, primarily the ability to retain liquid in the absorbent structure. In this method, corresponding test specimens of foam material are used, which already have absorbed liquid in connection with measurement of acquisition time. A tared filter paper is placed on top of a wet (after measuring acquisition time) test specimen, whereafter a weight which provides a load of 2.5 kPa is placed on top of the filter paper. After 15 seconds, the weight as well as the filter paper are removed, wherein the filter paper is weighed in order to record the liquid quantity which has been released from the test specimen and absorbed by the filter paper. Rewetting is presented in the unit g.

Vertical wicking, is measured in the way disclosed in the above-mentioned WO 93/04092, by means of recording the time consumed for absorbing a liquid, in this case synthetic urine, to 5 cm height in a strip of foam material. The result is presented in seconds.

Sinking time, is determined by means of recording the time in seconds which is consumed for a circular test specimen (diameter 2.9 cm) of the foam material to sink below the liquid surface in a container with synthetic urine.

Synthetic urine was used as absorption liquid when evaluating the absorption properties of the different foam materials if nothing else is stated. The synthetic urine, which was used when testing the foam materials, was a salt solution comprising different salts, and intended to imitate the chemical composition of human urine. In principle, similar testing result could be obtained by using any one of the, to the skilled person, well-known types of synthetic urine. The testing results which were obtained when testing the foam materials from trials 1 to 5 are evident from the following tables 1 and 2.

TABLE 1

| Trial/ Surfactant system | Density (g/cm³) | Pore-volume (g/g) | Compression resistance RTCD (%) | Initial abs. 0.3 ml (S) |
|---|---|---|---|---|
| Trial 1 | | | | |
| 3 ml SPAN 80 1 ml SPAN 85 | 0.066 | 20.3 | 40.3 | 3–60 |
| Trial 2 | 0.05 | 22.3 | 23 | 2.9 |
| 3 ml Atlox | 0.06 | 16.2 | 34 | 5.2 |
| Trial 3 | | | | |
| 2 ml Atlox | 0.20 | 5.7 | 33 | 2.4 |
| 1.5 ml SPAN 80 0.5 ml SPAN 85 | 0.12 | 7.0 | 27 | 6.2 |
| Trial 4 | | | | |
| 1 ml Atlox 2.25 ml SPAN 80 0.75 ml SPAN 85 | 0.07 | 13.9 | 42 | 2.2 |
| Trial 5 | | | | |
| 3 ml Atlox 3 ml SPAN 80 1 ml SPAN 85 | 0.16 | 6.8 | 30 | 9.2 |

As is evident from table 1, the foam material from trial 2, prepared by means of using solely a nonionic block copolymer with the trademark Atlox as an emulsifying agent, obtained properties close to the level which the conventional foam material from trial 1 exhibits. The foam material from trial 2 is according to a preferred embodiment of the invention.

From table 1 it is further evident that also the foam materials from trials 3–5, which were prepared by means of using a mixture of conventional surfactants (SPAN 80 and 85) and nonionic block co-polymer as emulsifying agent, obtained interesting properties. These foam materials illustrate advantageous embodiments of the invention.

From the following table 2, it is evident that the ability of repeated liquid absorption, measured as acquisition time 3×60 ml, was at least equal for the foam material according to the invention (trial 2), as for the foam material according to prior art (trial 1).

TABLE 2

| Acquisition time 3 × 60 ml, minutes - 10 minutes between each acquisition dose | | | |
|---|---|---|---|
| | Acquis. 1 | Acquis. 2 | Acquis. 3 |
| Trial 1 (prior art) | 2.1 | 6.6 | 12.8 |
| Trial 2 (acc. to the invention) | 0.4 | 8.6 | 11.4 |

| Rewetting, g - measured on corresponding specimens as acquisition time 3 × 60 ml | | | |
|---|---|---|---|
| | Rewet. 1 | Rewet. 2 | Rewet. 3 |
| Trial 1 (prior art) | 0.7 | 2.3 | 36.3 |
| Trial 2 (acc. to the invention) | 0.9 | 5.7 | 10.5 |

| Sinking time and vertical wicking, seconds (double tests) | | |
|---|---|---|
| | Sinking time | Vertical wicking |
| Trial 1 (prior art) | 27.9/43.3 | 607/600 |
| Trial 2 (acc. to the invention) | 16.5/90.3 | 337/318 |

Table 2 further shows that the rewetting for the material according to the invention (Trial 2) is approximately comparable to the foam material according to prior art (Trial 1) in one, and in two rewettings, whereas the rewetting in the third rewetting is clearly lower for the foam material according to the invention.

Table 2 also shows that the foam material according to the invention (Trial 2) has a comparable sinking time and a faster vertical wicking than the foam material according to prior art (Trial 1).

Trials 6–9

In these trials, two foam materials according to prior art were prepared in Trials 6 and 7, in a corresponding way as in Trial 1, whereas two foam materials according to a preferred embodiment of the invention were manufactured in Trials 8 and 9, in a corresponding way as the foam material in Trial 2.

The prepared foam materials were evaluated with regard to acquisition time, wherein the foam materials were washed with distilled water and dried in a heated air dryer between each liquid addition and measurement of acquisition time. In a first measurement series 1, acquisition times for foam material specimens from trials 6, 7 and 8 were recorded at five batch-wise additions of 5 ml synthetic urine (5×5 ml). In a second measurement series 2, acquisition times of the foam materials from Trials 6, 7, 8 and 9 were recorded at 6 batch-wise additions of 5 ml synthetic urine (6×5 ml). The obtained testing results for the foam materials from Trials 6–9 are evident from the following table 3.

TABLE 3

| MEASUREMENT | Acquisition time 5 × 5 ml, seconds | | | | |
|---|---|---|---|---|---|
| SERIES 1 | #1 | #2 | #3 | #4 | #5 |
| Trial 6, acc. to prior art | 10 | 25 | 13 | 37 | 101 |
| Trial 7, acc. to prior art | 21 | 13 | 17 | 101 | 200 |
| Trial 8, acc. to | 14 | 9 | 21 | 33 | 43 |

TABLE 3-continued

| the invention MEASUREMENT | Acquisition time 6 × 5 ml, seconds | | | | | |
|---|---|---|---|---|---|---|
| SERIES 2 | #1 | #2 | #3 | #4 | #5 | #6 |
| Trial 6, acc. to prior art | 82 | 18 | 27 | 96 | 136 | >300 |
| Trial 7, acc. to prior art | 7 | 6 | 34 | 98 | 84 | >300 |
| Trial 8, acc. to the invention | 10 | 27 | 75 | 59 | 89 | 144 |
| Trial 9, acc. to the invention | 7 | 13 | 7 | 37 | 30 | 50 |

It is clearly evident from the results that foam materials according to the invention maintain their hydrophilic character to a great extent also when the foam material specimens are subjected to a washing with distilled water and a heated-air drying between each measurement of acquisition time.

As mentioned above, the reason why the foam materials according to the invention, even in repeated wettings and dryings, maintain their hydrophilic character in a better way than foam materials according to prior art is the chemical structure of the foam surfactant, being used as a combined emulsifying and hydrophilizing agent according to the invention.

The chemical structure of the surfactant makes it possible to retain a sufficient proportion of the emulsifying agent in the foam material also after repeated wettings, something which renders the foam material according to the invention to be highly, permanently hydrophilic.

It has to be understood that the volumes of different raw materials and other trial conditions disclosed in the embodiments should be seen as conceivable examples of what makes it possible to practise the invention and that an industrial production of foam material according to the invention requires an adaption to the prevailing conditions. However, such an adaption is fully feasible for a man skilled in the art.

The present invention should not be regarded as being limited to what has been disclosed herein by means of the above-described examples, tables or the attached drawings, but its scope is defined by the attached claims.

What is claimed is:

1. A foam material for absorption of aqueous liquids, comprising a polymeric foam structure which is elastically formable, said foam structure comprising a plurality of cells formed by a plurality of internal surfaces of said foam structure, wherein said cells essentially are open and essentially in connection with each other when absorption of liquid is initiated, wherein the foam structure in connection to the internal surfaces comprises a surfactant which is a nonionic block copolymer, wherein said surfactant comprises poly(12-hydroxy-stearic acid), and that said internal surfaces essentially are hydrophilic.

2. A foam material according to claim 1, wherein the poly(12-hydroxy-stearic acid) forms a part of a mixture of surfactants.

3. A foam material according to claim 1, comprising a glass-like polymer component and a rubber-like polymer component,
    wherein the glass-like polymer component comprises styrene, and that the rubber-like polymer component comprises 2-ethylhexyl acrylate.

4. A foam material according to claim 1, wherein the foam material comprises a cross-linking agent, wherein said cross-linking agent comprises a divinyl compound.

5. A foam material according to claim 4, wherein the divinyl compound comprises a divinylbenzene.

6. A method of manufacturing a foam material for absorption of aqueous liquids, comprising emulsifying an oil phase and a water phase, using an emulsifying agent in order to form a stable emulsion, wherein the volume of said oil phase is smaller than the volume of said water phase, said oil phase comprising a first polymerizable monomer with glass-like properties, a second polymerizable monomer with rubber-like properties, and a cross-linking agent, while said water phase comprises an initiator and an electrolyte, whereafter said monomers in the essentially continuous oil phase of the stable emulsion are polymerized in order to form a polymeric foam structure which is elastically formable and comprises a plurality of cells having a plurality of internal surfaces, wherein the emulsifying agent added during emulsifying comprises a surfactant which is a nonionic block copolymer, wherein said surfactant comprises poly(12-hydroxy-stearic acid), and that the foam material is dewatered after the polymerization and thereby provides said internal surfaces which have been rendered hydrophilic by said surfactant.

7. A method according to claim 6, wherein the poly(12-hydroxy-stearic acid) form a part of a mixture of surfactants.

8. A method according to claim 6
    wherein the foam material is subjected to a washing treatment after polymerization is completed.

9. A method of using a foam material for absorbing an aqueous body fluid, comprising contacting a foam material with an aqueous body fluid, wherein the foam material comprises essentially hydrophilic, internal surfaces and a surfactant which is a nonionic block copolymer wherein said surfactant comprises poly(12-hydroxy-stearic acid).

10. A method of using a foam material according to claim 9, wherein the poly(12-hydroxy-stearic acid) forms a part of a mixture of surfactants.

11. An absorbent disposable article, comprising an absorption core, surface material and elastic means, wherein the absorption core comprises a foam material with a polymeric foam structure, which in connection to its internal surfaces comprises a surfactant which is a nonionic block copolymer, wherein said surfactant comprises poly(12-hydroxy-stearic acid), and that said internal surfaces are essentially hydrophilic.

12. An absorbent disposable article according to claim 11, wherein the poly(12-hydroxy-stearic acid) forms a part of a mixture of surfactants.

13. An absorbent disposable article according to claim 11, said article being delivered in a transport package to a wearer,
    wherein cells inside the polymeric foam structure of said foam material essentially are in a compressed position when the absorbent article is inside said transport package, and that said cells essentially are in an expanded position when the absorbent disposable article is in contact with the skin of the wearer, and that said cells are essentially open and stand in connection with each other when absorption of aqueous liquid initiated.

* * * * *

UNITED STATES PATENT AND TRADEMARK OFFICE
CERTIFICATE OF CORRECTION

PATENT NO. : 6,040,494
DATED : March 21, 2000
INVENTOR(S) : KALENTUN et al.

It is certified that error appears in the above-indentified patent and that said Letters Patent is hereby corrected as shown below:

Column 16, line 62, before "initiated" insert --is--.

Signed and Sealed this

Twenty-fourth Day of April, 2001

Attest:

NICHOLAS P. GODICI

*Attesting Officer*       *Acting Director of the United States Patent and Trademark Office*